United States Patent
Fircho et al.

(10) Patent No.: US 8,846,130 B2
(45) Date of Patent: Sep. 30, 2014

(54) IMPLANT AND METHOD FOR PRODUCING THE SAME

(75) Inventors: Horst Fircho, Koesterbeck (DE); Ullrich Bayer, Admannshagen-Bargeshagen (DE); Frank Endres, Clausthal-Zellerfeld (DE)

(73) Assignee: Biotronik AG, Buelach (CH)

( * ) Notice: Subject to any disclaimer, the term of this patent is extended or adjusted under 35 U.S.C. 154(b) by 163 days.

(21) Appl. No.: 13/219,023

(22) Filed: Aug. 26, 2011

(65) Prior Publication Data

US 2012/0053679 A1    Mar. 1, 2012

Related U.S. Application Data

(60) Provisional application No. 61/377,474, filed on Aug. 27, 2010.

(51) Int. Cl.
| | |
|---|---|
| *B05D 3/10* | (2006.01) |
| *C25D 5/18* | (2006.01) |
| *C25D 11/18* | (2006.01) |
| *A61L 31/02* | (2006.01) |
| *A61L 31/08* | (2006.01) |

(52) U.S. Cl.
CPC ........... *A61L 31/022* (2013.01); *A61L 2400/18* (2013.01); *A61L 31/088* (2013.01)
USPC ......... 427/2.24; 427/2.25; 205/107; 205/318; 205/322

(58) Field of Classification Search
None
See application file for complete search history.

(56) References Cited

U.S. PATENT DOCUMENTS

| | | | | |
|---|---|---|---|---|
| 2006/0229711 A1* | 10/2006 | Yan et al. | ...................... | 623/1.38 |
| 2008/0081212 A1* | 4/2008 | Inbe et al. | ...................... | 428/651 |
| 2008/0086195 A1* | 4/2008 | Atanasoka et al. | .......... | 623/1.15 |
| 2010/0087914 A1* | 4/2010 | Bayer et al. | .................. | 623/1.39 |

\* cited by examiner

*Primary Examiner* — Cachet Sellman
(74) *Attorney, Agent, or Firm* — Wagenknecht IP Law Group PC

(57) ABSTRACT

An implant and method for producing an implant, in particular an intraluminal endoprosthesis, with a body, wherein the body contains iron or an iron alloy, comprising the following steps:
a) providing the implant body (1),
b) applying a metallic coating comprising as main constituent at least one element of the group containing tantalum, niobium, zirconium, aluminum, magnesium, vanadium, molybdenum, hafnium, and wolfram onto at least a portion of the body surface, and
c) plasmachemical treatment of the portion of the body surface provided with the coating in an aqueous solution for producing a plasmachemically generated layer (3, 5, 7) by means of applying a plasma-generating pulsating voltage to the body of the implant, wherein the pulsating voltage has sufficient energy that the metallic coating (3, 5, 7) is temporarily and sectionally ionized up to the underlying implant body (1) in such a manner that the generated layer has pores (5) which extend at least partially up to the implant body.

12 Claims, 3 Drawing Sheets

IMPLANT AND METHOD FOR PRODUCING THE SAME

CROSS REFERENCE TO RELATED APPLICATIONS

This invention claims benefit of priority to U.S. patent application Ser. No. 61/377,474 filed Aug. 27, 2010; the contents of which are herein incorporated by reference in their entirety.

TECHNICAL FIELD

The present invention relates to a method for producing an implant, in particular an intraluminal endoprosthesis, with a body, wherein the body contains iron or an iron alloy, and to an implant obtainable or obtained by such a method.

BACKGROUND

Medical endoprostheses or implants for a wide range of applications are known in a large variety from the prior art. Implants in the meaning of the present invention are to be understood as endovascular prostheses or other endoprostheses, for example stents, fastener elements for bones, for example screws, plates or nails, surgical sutures, intestinal staples, vascular clips, prostheses in the region of the hard and soft tissue, and anchor elements for electrodes, in particular of pacemakers or defibrillators.

Today, particularly frequently used as implants are stents which serve for the treatment of stenoses (vasoconstrictions). Stents have a body in the form of an open-worked tubular or hollow-cylindrically basic grid which is open at both longitudinal ends. The tubular basic grid of such an endoprosthesis is inserted into the vessel to be treated and serves for supporting the vessel. Stents are established in particular for the treatment of vascular diseases. By using stents or other implants, constricted areas in the vessels can be expanded, thereby resulting in a lumen gain. By using stents or other implants, an optimal vessel cross-section, which is primarily necessary for the success of the therapy, can be achieved; however, the permanent presence of such a foreign body initiates a cascade of microbiological processes which can result in a gradual constriction of the stent, and in the worst case in a vascular occlusion.

An approach for the solution of this problem is to produce the stent or other implants from a biodegradable material.

Biodegradation is to be understood as hydrolytic, enzymatic and other metabolic-related degradation processes in a living organism which are mainly caused by body liquids which get in contact with the biodegradable material of the implant and which result in a gradual degradation of the structures of the implant containing the biodegradable material. Through this process, the implant loses its mechanical integrity at a certain point in time. As a synonym for the term biodegradation, the term biocorrosion is frequently used. The term bioresorption comprises the subsequent resorption of the degradation products by the living organism.

Suitable materials for the body of biodegradable implants can contain, for example, polymers or metals. The body can consist of a plurality of said materials. A common feature of said materials is their biodegradability. Examples for suitable polymeric compounds are polymers from the group cellulose, collagen, albumin, casein, polysaccharides (PSAC), polyactide (PLA), poly-L-lactide (PLLA), polyglycol (PGA), poly-D,L-lactide-co-glycolide, (PDLLA-PGA), polyhydroxybutyrate (PHB), polyhydroxyvaleric acid (PHV), polyalkyle carbonate, polyorthoester, polyethylene terephthalate (PET), polymalonic acid (PML), polyanhydrides, polyphosphazenes, polyamino acids and their co-polymers, and hyalaronic acid. The polymers can be available depending on the desired properties in pure form, in derivatized form, in the form of blends, or as co-polymers.

The present invention relates to implants made of a metallic biodegradable material based on iron or iron-based alloys (hereinafter in short: iron alloy).

Already known are stents which have coatings with different functions. Such coatings serve, for example, for releasing drugs, arranging a x-ray marker, or for protection of the underlying structures.

When implementing biodegradable implants, the degradability is to be controlled according to the intended therapy or the application of the respective implant (coronary, intracranial, renal, etc.). For many therapeutic applications it is, for example, an important target corridor that the implant loses its integrity within a time period of four weeks to six months. Here, integrity, i.e., mechanical integrity, is to be understood as the property that the implant barely experiences any mechanical shortcomings with respect to the non-degradable implant. This means that the implant is mechanically stable such that, for example, the collapse pressure has dropped only insignificantly, i.e., not below 80% of the nominal value. Thus, with existing integrity, the implants still meet its main function which is to keep the vessel open. Alternatively, integrity can be defined in that the implant is mechanically stable such that it is barely subject of any geometrical changes in its loaded state in the vessel, for example, does not collapse significantly, i.e., shows under load at least 80% of the dilatation diameter or, in case of a stent, has barely any partially fractured supporting webs.

Implants with an iron alloy, in particular ferrous stents, are producible in a particularly inexpensive and simple manner. However, for example for the treatment of stenoses, these implants lose their mechanical integrity or supporting effect only after a relatively long period of time, i.e. only after a retention period in the treated organism of approximately 2 years. This means that the collapse pressure for ferrous implants decreases too slow over time for the desired applications.

In the prior art, different mechanisms for controlling degradation of implants have already been described. They are based, for example, on inorganic or organic protection layers or their combinations which resist the human corrosive environment and the corrosion processes taking place therein. Previously known solutions are characterized in that barrier layer effects are achieved which are based on a spatial and preferably defect-free separation of the corrosion medium from the metallic medium. Said effects result in that the degradation time is extended. Thus, the degradation protection is ensured through differently composed protection layers and by defined geometrical distances (diffusion barriers) between the corrosion medium and the basic magnesium material. Other solutions are based on specifically changing alloying constituents of the biodegradable material of the implant body. However, with the aforementioned solutions it is in most cases not possible to bring the dissolution initiated by the degradation process and the resulting web breakages into the desired time window. The consequence, in particular in case of implants containing an iron alloy, is a degradation that starts too late, or an excessive variability of the degradation of the implant.

Another problem in connection with coatings is the fact that stents or implants normally assume two different states, namely a compressed state with a small diameter and an expanded state with a larger diameter. In the compressed state, the implant can be inserted by means of a catheter into the vessel to be supported and can be positioned at the position to be treated. At the site of treatment, the implant is then dilated, for example by means of a balloon catheter. Due to the diameter change, the body of the implant is subjected here to a heavy mechanical load. Further mechanical loads on the implants can occur during the production of the implant or during movement of the implant in or with the vessel in which the implant is inserted. The above mentioned coatings thus have the disadvantage that a coating breaks during the deformation of the implant (e.g. formation of micro cracks) or is partially removed. Hereby, an unspecified local degradation can be caused. Moreover, the start and the speed of the degradation depend on the size and the distribution of the micro cracks generated by the deformation, which, as defects, are difficult to control. This results in a high variance of the degradation times.

From the printed publications US 2008/0086195 A1 and WO 2008/045184 A1, a medical device such as a catheter or a stent is known on which a polymer-free coating is applied by means of a plasma electrolytic deposition (PED). The plasma electrolytic coating is used for introducing additional active ingredients into the coating which contain a drug or a therapeutic agent. The plasma electrolytic coating comprises a plasma electrolytic oxidation (PEO), a micro-arc oxidation (MAO), a plasma-arc oxidation PAO), an anodic spark oxidation, and a plasma electrolytic saturation (PES). The plasma electrolytic treatment includes the use of different electrical potentials between the medical device and a counter electrode which generates an electrical discharge (a spark or arc plasma micro discharge) on the surface or near the surface of the medical device and which does not cause a significant extension of the degradation times. Thus, the method disclosed in the above mentioned printed publications does not solve the above mentioned problem.

SUMMARY

It is therefore the object of the present invention to provide a cost-effective method for producing an implant which method effects a degradation of the implants containing iron or an iron alloy within the desired time window, in particular within a shorter time period. For this purpose, the degradation has to take place at a controllable point in time. Accordingly, the object of the invention is also to provide such an implant.

The object mentioned above is solved by a method comprising the following steps:
a) Providing the implant body,
b) applying a metallic coating comprising as main constituent at least one element of the group containing tantalum, niobium, zirconium, aluminum, magnesium, vanadium, molybdenum, hafnium, and wolfram onto at least a portion of the body surface,
c) plasmachemical treatment of the portion of the body surface provided with the coating in an aqueous solution for producing a plasmachemically generated layer by means of applying a plasma-generating pulsating voltage to the body of the implant, wherein the pulsating voltage has sufficient energy that the metallic coating is temporarily and sectionally ionized up to the underlying implant body in such a manner that the generated layer has pores which extend at least partially up to the implant body.

In the method according to the invention, first, a metallic coating comprising one or more valve metals such as tantalum, niobium, zirconium, aluminum, magnesium, vanadium, molybdenum, hafnium and/or wolfram, preferred tantalum, niobium and/or zirconium, is applied onto the body surface of the implant body. After that, a plasmachemical treatment is carried out in such a manner that pores are generated in the metallic coating which penetrate through the metallic coating and reach up to the surface of the implant body. This means that the pores have approximately a depth that corresponds to the layer thickness of the metallic coating according to step b). Thus, an ionization is carried out up to the base material which contains iron or an iron alloy, wherein the pores are arranged at geometrically regular distances.

The pores are always generated where the lowest breakdown voltage of the valve metal layer exists and where consequently the plasma process is ignited. Once these zones are coated, surface areas follow seamlessly which, among other things, because of the geometry, have a higher density of flux lines. However, depending on the actual coating conditions, a reversed sequence in the course of the plasma generation is also possible.

The regularity of the pore distances is based on the fact that each of the areas in which plasma is ignited always represents the weak point with respect to the dielectric strength. The immediate vicinity of a pore, due to the primarily oxidic/phosphatic layer composition, can be designated as plasma-resistant. Only at a certain distance from the edge of an already generated pore (ca. 1 to 3 µm), the metallic portion of the coating material increases again and, subsequently, a plasmachemical oxidation of these zones takes place. At a voltage with an upper limit (final voltage) and a constant current density, this "gridding" of the surface takes place until said regularity in the pore structure is obtained. After this, the current drops rapidly. When approximately 20% of the output current density is reached, the coating process can be stopped by manually interrupting the current flow.

The plasmachemically generated layer is to be understood as the layer formed by the plasmachemical method from the metallic coating, a volume of the base material arranged on the surface of the implant body, and the pores. Further, "a pore extending through the plasmachemically generated layer" is to be understood such that a thin, maximum 200 nm thick pore bottom layer, which is visible in a micrograph, covers the surface of the base material of the implant body. Said pore bottom layer prevents that the electrolyte, upon contact with the base material of the implant body, does not disturb the plasmachemical process. Therefore, the electrical parameters are to be selected in such a manner that the energy input during the plasma effect extends towards the base material only up to a distance of maximum 0.5 µm. This has the effect that the pore bottoms are formed by oxides and phosphates of the coating material and a small proportion of oxides and phosphates of the base material of the implant body, for example a small proportion of oxides and phosphates of an iron-based alloy. Thus, there is no purely metallic implant body material at the pore bottom. The thickness of the layer consisting of mixed oxides and mixed phosphates from the coating material and the base material at the pore bottom is between approximately 10 nm and 200 nm.

During the plasmachemical treatment, the body surface is treated in an aqueous electrolyte system (aqueous solution) and the plasmachemical effects are generated directly on the surface of the metallic coating. The plasma, which is stable for microseconds on the surface of the metallic coating, generates reaction products which result in the formation of the pores in the metallic coating. Also, in this connection, the metallic coating is partially transferred and a part of the near-surface layer of the underlying implant surface is transferred. Accordingly, the microporous or perforated layer generated through the plasmachemical treatment has a plurality of phases with respect to its chemical composition. On the surface of the plasmachemically generated layer are oxides, phosphates and/or hydroxides of the elements of the metallic coating, in particular of the tantalum, and/or niobium, and/or zirconium. Arranged underneath are the remains of the metallic coating applied in step b). In the area of the pore bottom, iron compounds, iron oxides, and/or iron phosphates as well as the oxides and phosphates of the respective coating metals can be found. Underneath there is the original material of the implant body.

The body of the implant comprises at least a part of the implant, preferably the main part of the implant which provides for the mechanical integrity of the implant. The present invention relates in particular to implants, the body of which contains iron as main constituent and is preferably biodegradable.

An essential advantage of the method according to the invention over the prior art is that through the high energy of the pulsating voltage (also called pulse voltage) generating the plasma, the metallic coating as well as an underlying area of the implant body are temporarily and sectionally ionized. Here, the voltage increases from initially 0 V over a time period of approximately 3 μs up to a peak voltage and drops parabolically within the following 2 μs. The peak voltage is increased from pulse to pulse up to a maximum value which lies at around 500 V. However, due to the inertia of the system (electrolyte, electrodes, mechanical inertia of the charge carriers in the electrolyte), after passing the peak voltage, the voltage does not go back to zero but only to a minimum value. After this, the voltage increases again up to the next peak voltage, etc. Through the plasma generated in this manner, the metallic coating is sectionally ionized so that pores are created or the metallic coating is perforated. At the pore bottom, the implant body material or the metallic coating is partially ionized to a certain depth which depends on the specific energy of the pulsating voltage. Hereby, a tight material bond between the implant body and the plasmachemically generated layer is created which results in a high adhesive strength of the layer arranged on the implant body surface. The plasmachemically generated layer with the constituents of the metallic coating is, in a way, sectionally alloyed into the surface of the implant body. This results in that the plasmachemically generated layer, even at high mechanical load on the implant according to the invention, for example during the stent dilatation, does not delaminate from the implant body. Thus, the degradation takes place in a more controllable and uniform manner since a defined access of the electrolyte to the material of the implant body exists only in the area of the pores. It is of advantage here if the distribution of the pores is uniform. At places where no pores are arranged and upon contact with the body liquid, the plasmachemical layer acts as a temporary corrosion protection which causes a delayed degradation.

The energy is a product formed from the bath voltage U and the current I or a product formed from current density and pulse length. Preferably, for the plasmachemical treatment, energies in the range of 0.6 Ws to 8 Ws are used, and particularly preferred for implants, preferably stents, containing an iron alloy, the range of energy is between 1 Ws and 3 Ws. The specified energy values apply in particular for implants with a total surface area in the order of approximately 100 mm$^2$.

For example, with a mean bath voltage of 400 V (maximum value of the peak voltage here is 500 V), a current density of 1 A/dm$^2$=10 mA/cm$^2$, a pulse duration of 5 μs, and 1000 μs pulse pause (results in a factor of 0.005), and a coating time of 1 minute, the following energetic relationship is given:

Implant surface of a stent approximately 100 mm$^2$=0.01 dm$^2$

Coating energy $W=U_{eff} \cdot I \cdot t_{eff}$

=400 V·0.01 dm$^2$·1 A/dm$^2$·60 s·0.005(pulse on/off)

=1.2 Ws

Thus, the surface of an implant such as, e.g. a stent with a surface of approximately 100 mm$^2$ is plasmachemically surface-treated with a coating energy of at least 0.6 wattseconds.

It is further of advantage that the process-related porous structure of the plasmachemically generated layer has a high plastic deformability. For example, the micro-cracks generated when dilating a stent are stopped in the pores adjacent to the micro-cracks by energy accumulation or energy dissipation. Thus, a delamination of the plasmachemically generated layer does not take place.

If desired, yet another, e.g. polymeric coating can be applied on the plasmachemically generated layer. Due to the pore structure, a good adhesion of the additional coating on the plasmachemically generated layer is provided.

Moreover, the pore structure of the plasmachemically generated layer can function as substance reservoir for pharmaceutically active substances which can be incorporated as nano or micro particles and can serve as lubricants for reducing the friction coefficient within the catheter, bone growth-stimulating substances such as calcium phosphate, temporarily acting contrast agents, or cell growth-inhibiting, radioactive substances.

A "pharmaceutically active substance" (or therapeutically active or effective substance) in the meaning of the invention is to be understood as plant- or animal-based active agent or a synthetic active substance (medicament), or a hormone, which is used in a suitable dosage as therapeutic agent for influencing conditions or functions of the body, as substitution for naturally generated active agents in human or animal bodies such as insulin, and for eliminating pathogens, tumors, cancer cells or substances foreign to the body, or for rendering them harmless. The release of the substance in the environment of the implant has a positive effect on the healing process or acts against pathological changes of the tissue due to the surgical intervention or serves for rendering sick cells harmless in oncology.

Such pharmaceutically active substances have, for example, an anti-inflammatory and/or anti-proliferative and/or spasmolytic effect, whereby, for example, restenoses, inflammations or (vascular) spasms can be prevented. Such substances can, for example, consist of one or more substances of the active agent group of calcium channel blockers, lipid regulators (such as, for example, fibrates), immunosuppressive agents, calcineurin inhibitors (such as, for example, tacrolimus), antiphlogistics (such as, for example, cortisone or diclofenac), anti-inflammatory agents (such as, for example, imidazoles), antiallergics, oligonucleotides (such as, for example, dODN), estrogens (such as, for example, genistein), endothelium formers (such as, for example, fibrin), steroids, proteins, hormones, insulines, cyrostatic drugs, peptides, vasodilatators (such as, for example, sartanes) and anti-proliferatively acting substances, taxoles or taxanes, here preferably paclitaxel or sirolimus.

Also, due to the anodic functional principle of the plasmachemical coating, there is no danger of hydrogen embrittlement of the implant material. There is also no danger of mechanical damage of the implant body material since the roughening of the surface is not carried out in a mechanical manner.

A further advantage of the method according to the invention is that non-removable surface contaminations of the base material are absorbed by the plasmachemically generated layer and thus do not have an additional influence on the degradation process. Moreover, depositions of the implant body (for example non-dissolved alloying constituents), which can be sharp-edged and protrude from the surface, are covered. This results also in an increased hemo- or bio-compatibility.

Due to the existence of the plasmachemically generated layer produced by means of the method according to the invention, the storage and transport conditions for the implants produced according to the method according to the invention are simplified because, under storage conditions and in the mounted and sterilized state, the stability with respect to degradation of such an implant is higher than for non-coated implants.

In a preferred exemplary embodiment, the layer thickness of the metallic coating after completion of step b) is 0.1 µm to 1.5 µm. The mentioned thickness of the metallic coating is selected such that the metallic coating, including the underlying material of the implant body, can be sectionally and temporarily ionized by means of implementable plasmachemical oxidation effects. In addition, the degradation speed can be controlled by varying the layer thickness. This opens up the possibility to adapt the degradation duration of the implant to the specific implantation site (coronary, intracranial, renal, etc).

It is further of advantage if the metallic coating is applied by means of an ionic liquid. This is a particularly simple method to uniformly coat all parts of the surface of the implant body, even undercuts.

Alternatively, PVD and CVD methods (such as, e.g. sputtering or thermal evaporation) for applying the metallic coating can also be used. However, when using these methods and if iron is used as material for the implant body, a temperature of approximately 400° C. at a treatment time of 30 minutes must not be exceeded. This would otherwise result in irreversible changes of the mechanical properties (softening). However, coating by means of PVD or CVD methods by means of an ionic liquid has the disadvantage that no uniform covering of the implant surfaces, which often have a complex shape, takes place. Thus, PVD or CVD methods are in particular suitable for implants which have structures or designs that are shaped in a simple manner.

In contrast, the coating by means of ionic liquids can be used for complexly shaped implants having undercuts, cavities and/or blind holes. Such a coating method allows the implementation of a uniform layer thickness even on complex shapes (e.g. inside of stents) and thus contributes significantly to a uniform degradation behavior after the plasmachemical treatment.

In a development of the invention, besides the at least one valve metal, the metallic coating comprises in addition an element of the group copper and silver. Here, the total percentage of the elements copper and silver in the material of the metallic coating should not be more than 15% by mass, preferably not more than 11% by mass. In particular, the content of silver and/or copper is selected such that the ratio of the content valve metal to silver or copper lies outside of the solubility limit of the respective binary system. Through the plasmachemical treatment, dissolved silver or copper is created in the matrix of the valve metal, or metallic copper and/or silver on the surface of the plasmachemically generated layer. The metallic portion acts antiproliferative when in contact later with the cells of the body of the treated person. Here, the portion of the metallic silver and/or copper in the material of the plasmachemically generated layer is less than 5% by mass.

In a further exemplary embodiment, the implant is rinsed after the plasmachemical treatment in a solvent, preferably distilled $H_2O$, and after this, preferably dried at a temperature of at least 80° C., particularly preferred at least approximately 100° C., wherein the drying is preferably carried out in a convection oven. This procedure results in the residue-free removal of compounds of the plasmachemical electrolytes from the implant surface. The drying at increased temperatures ensures also that potential electrolyte residues which adhere longer due to capillarity action (e.g. in the filigree surface shape of a stent), do not initiate undesired reactions with the implant surface.

In a preferred exemplary embodiment, the aqueous solution used during the plasmachemical treatment contains $Sr^{2-}$ ions, which are preferably contained in the aqueous solution in each case in a concentration of 0.05 Mol/l to 2.0 Mol/l. Hereby, strontium compounds are formed in the plasmachemically generated layer. The same are advantageous because in particular strontium carbonate is sparingly water-soluble and thus forms a layer component which is particularly inhibiting for the degradation in the surface layer of the implant. In addition, in particular in cranial applications, the strontium carbonate contained in the coating can have a drug-like effect against cerebral sclerosis.

In a preferred exemplary embodiment of the method according to the invention, the aqueous solution used for the plasmachemical treatment contains in addition one or more ions selected from the group of phosphates, carbonates, hydroxides and silicates.

If the aqueous solution for the plasmachemical treatment contains phosphate ions, then, besides the oxides and hydroxides, also phosphates of the material of the metallic coating or the implant body are formed in the plasmachemically layer, which phosphates provide for a better biological compatibility of the implant material, in particular the coating. Here, the phosphate ion are made available by adding potassium dihydrogen phosphate, and/or dipotassium hydrogen phosphate, and/or potassium phosphate, and/or sodium dihydrogen phosphate (dihydrate), and/or heptahydrate, and/or dodecahydrate to the aqueous electrolytes. The preferred concentration range here is between 5 g/l and 200 g/l of the added compound in the aqueous solution. A particularly preferred concentration is between 50 and 100 g/l of potassium dihydrogen phosphate.

To keep the pH-value of the electrolyte (aqueous solution) at a constant level, it is preferred that a buffer, preferably potassium dihydrogen phosphate and/or sodium dihydrogen phosphate, is contained in the aqueous solution.

In a further preferred exemplary embodiment, the implant body is electrochemically treated, preferably electrochemically polished, prior to applying the metallic coating. Hereby, the contaminations on the surface of the implant body are removed so that the application of the metallic coating or the plasmachemical treatment is carried out on a defined surface. It is important that the surface is free of contamination which would otherwise result in a poor adhesion of the plasmachemically generated layer. Electropolishing results in low-contamination surface layers due to high material removal effects (depth action).

Preferably, the plasmachemical treatment of the implant body is carried out in that to the body, a pulsed, preferably positive voltage is applied, the amplitude (peak voltage) of which during most of the treatment period exceeds at least approximately 400 Volt, particularly preferred at least approximately 450 Volt, and which preferably increases in the course of the treatment up to maximum approximately 500 V. The voltage curve corresponds to the curve designated above as pulsating voltage or pulse voltage.

By means of said high pulsed voltages with a pulse length of preferably maximum approximately 50 microseconds, particularly preferred approximately 5 microseconds, over a period of some microseconds, plasmas are generated on the surface of the implant body, which plasmas result in the reaction of the metallic material of the implant body with the electrolytes. Between the voltage pulses follows a rest phase of preferably ca. 1000 microseconds. The energy to be provided in the form of voltage pulses is at least ca. 0.6 Ws for an implant surface of 100 $mm^2$. For implant surfaces with a varying size, the minimum amount of energy changes proportionally to the surface area of the surface.

Preferably, the plasmachemical process is carried out with a current density of at least approximately 5 $mA/cm^2$, preferably at least approximately 10 $mA/cm^2$.

In a further preferred exemplary embodiment, after the plasmachemically generated layer, a further layer, preferably a polymer-containing layer (hereinafter referred to as fourth layer), particularly preferred containing at least one polymer of the group parylene, PLA (polyactide) and its copolymers, in particular PLLA (poly-l-lactide) and PLGA (poly(lactic-co-glycolic acid)) is applied. Preferred layer thicknesses of the further layer lie between approximately 0.5 and approximately 10 μm. Through such a layer combination, the degradation time of the implant can again be significantly increased. Also, the high gap penetration capability of parylene has an advantageous effect so that a deep penetration of the pores of the plasmachemically generated layer and/or the pore base layer down to the pore bottoms takes place by parylene. The characteristic permeation properties of PLA and parylene, in particular parylene N, for water, chloride-containing solutions, and hydrogen provide in connection with the underlying plasmachemically generated surface for a controllable degradation behavior of the implants. The same is also characterized by a corrosion proceeding uniformly and slowly over the implant cross-section. Moreover, the further layer contributes in addition to the prevention or hold-up of the crack propagation at mechanical load and prevents partial layer delaminations. It is particularly preferred if the further layer consists of parylene N or PLLA L210.

Here, parylene is the designation for fully linear, semi-crystalline, uncrosslinked aromatic polymers. The different polymers have different properties and can be divided into four basic types, namely parylene C, parylene D, parylene N and parylene F. For the use as further layer in the layer composite according to the invention, preferably parylene N is used.

The plasmachemically generated layer arranged underneath the further layer results in good adhesion properties of the polymer layer due to its porous structure so that a prior primer treatment, which would otherwise be necessary, becomes redundant.

The above object is further solved by an implant which is obtainable or obtained by an above described method according to the invention. Such an implant has the advantages described above in connection with the production method according to the invention.

According to the invention, the metallic coating has a layer thickness of 0.1 μm to 1 μm after completion of step b).

It has already been described above that the plasmachemically generated layer comprises pores, wherein the pores have a density of approximately 50,000 pores/$mm^2$ to approximately 250,000 pores/$mm^2$. It was found that within this pore density range still a good wetting of the pore bottom with blood or other body fluids (plasma) takes place, while at higher pore densities, the wetting effect would be so low that the corrosion could not proceed in an accelerated manner. Low pore densities below 50,000 pores/$mm^2$ would create an excessive notch effect. This means that the pores could not stop cracks during the dilatation of stents and that therefore the coating would delaminate over large areas.

In a development of the invention, the pores of the plasmachemically generated layer have a diameter of approximately 0.5 μm to approximately 5 μm, preferably approximately 1 μm to approximately 2 μm. Analog to the above explanations with respect to the pore density, large pores at a given area are equivalent to a low pore density. Accordingly, pores which are larger than the pores specified above would result in an increased notch effect.

The plasmachemically generated layer contains preferably a compound selected from the group containing phosphates, hydroxides and oxides of the material of the implant body and the material of the metallic layer, in particular phosphates, hydroxides and oxides of the iron, tantalum, niobium, zirconium, aluminum, magnesium, vanadium, molybdenum, hafnium, and/or wolfram.

Here, a compositional gradient from the surface of the implant into the depth to the transition of the plasmachemically generated layer into the material of the implant body is observed.

The advantage of tantalum or another valve metal as integral part of the metallic coating and thus as integral part of the plasmachemically generated layer is that these materials together with the iron arranged on the pore bottom form a local element, wherein the potential difference to the valve metal (compared to noble metals) resulting from the position of the iron in the electrochemical voltage series is relatively small so that the degradation process is not too fast and not too uncontrollable.

Another advantage of the implant according to the invention is that the formability of the implant, e.g. during dilatation, is improved. The reason for this is that there is a gradient of the modulus of elasticity from the outer surface of the implant according to the invention, thus from the outer surface of the plasmachemically generated layer, to the inside. Thereby, the mechanical stress between the implant surface and the neutral phase inside the component is considerably reduced.

The methods according to the invention are explained hereinafter by means of examples and figures. For this, all illustrated and/or described features form the subject matter of the invention, independent of their summary in the claims or their relations.

DETAILED DESCRIPTION

Example 1

A stent body made of an iron-based alloy (99.5% by mass iron, balance carbon) is manufactured by means of conventional methods such as laser cutting and electropolishing to a near net shape. Subsequently, the stent body is provided by means of an ionic liquid with a metallic coating consisting of tantalum and 10% by mass silver, wherein the layer thickness of the metallic coating is approximately 1 µm.

The coating of the stent body by means of an ionic liquid is implemented as follows. The electrolyte is an ionic liquid and is composed of 1-butyl-1-methylpyridinium, trifluoromethyl sulfamate, $TaF_5$, and silver trifluoromethyl sulfamate. The coating is carried out at a temperature of the ionic liquid of 100-250° C. The coating time is approximately 0.1 hours. The potentiostatic polarization is approximately −1oo mV to −1000 mV versus $Ta/TaF_5$.

Figure 1:
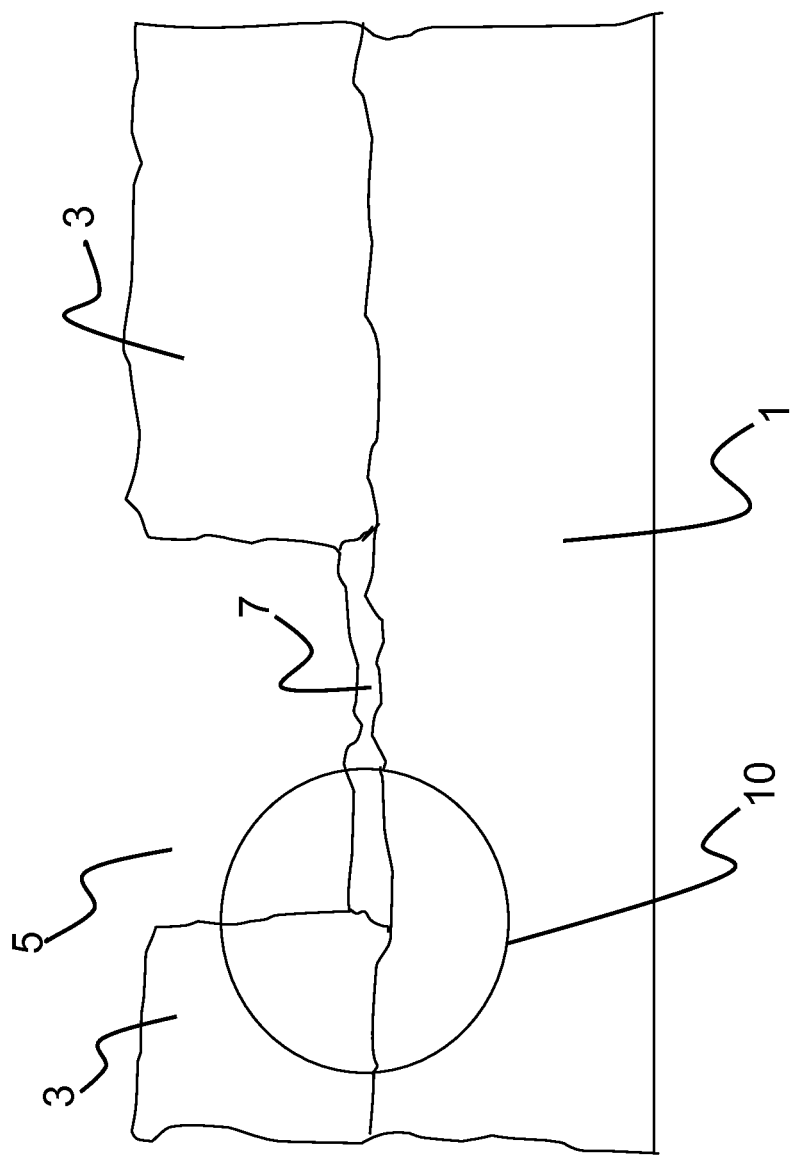
FIG. 1 shows a cross-section of the near-surface area of a web of a first exemplary embodiment of a stent according to the invention.

After this, a plasmachemical oxidation of the stent provided with the metallic coating is carried out in an aqueous, phosphate-containing electrolyte. This generates an approx. 1 µm thick, plasmachemically generated layer with regularly arranged pores with a diameter of approx. 1 µm to 2 µm and a pore density of 50,000 to 250,000 pores/mm$^2$. A cross-section of a web of a stent produced in such a manner is illustrated in FIG. 1.

Figure 2:
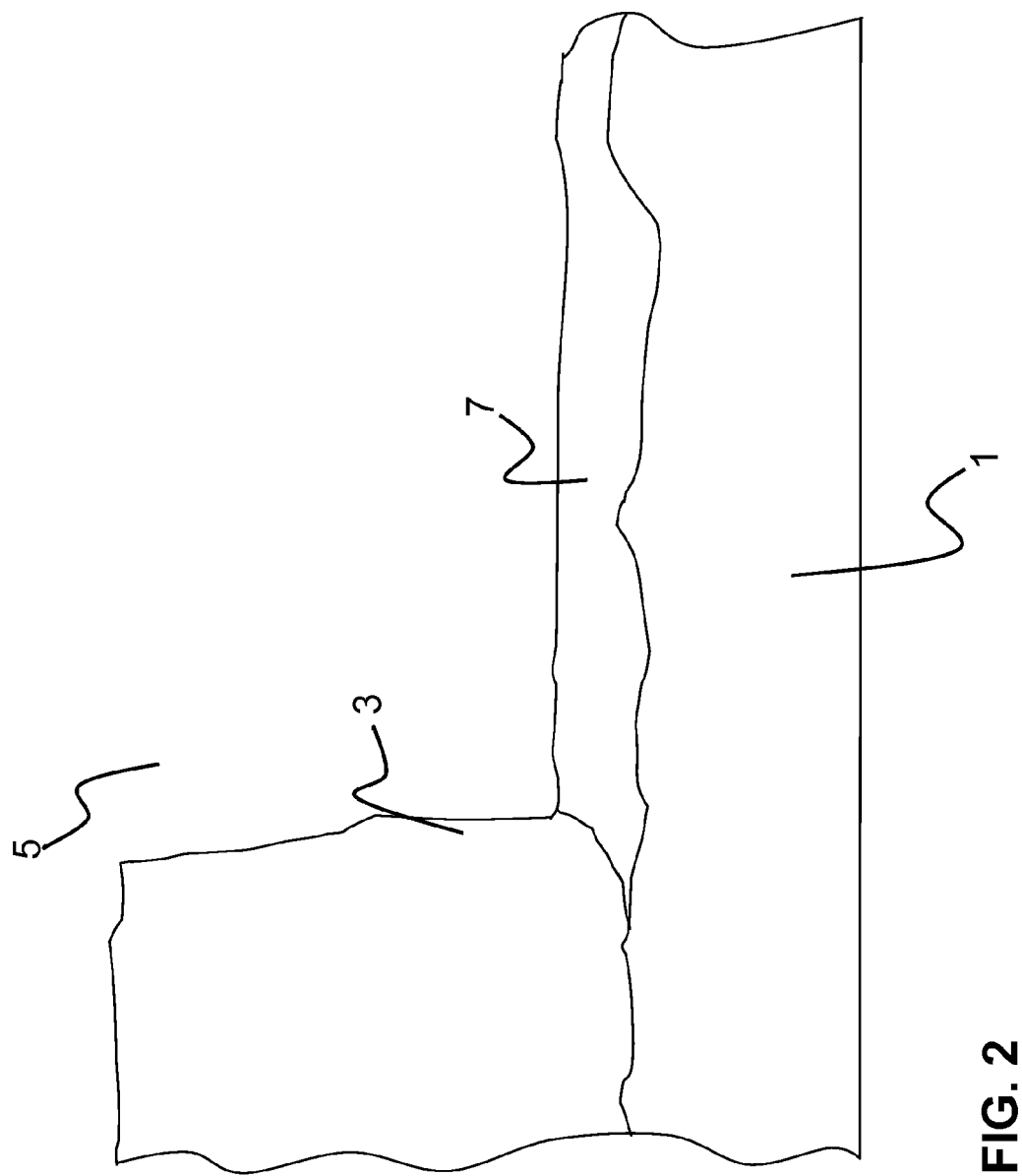
FIG. 2 shows an enlarged cut-out from the cross-section shown in FIG. 1.

On the implant body 1 made of the iron alloy, the plasmachemically generated layer 3 is arranged which has pores 5. The layer thickness of the plasmachemically generated layer 3 is approximately 1 µm. The pore 5 has a diameter of approx. 1.5 µm. The encircled cut-out 10 of the cross-section shown in FIG. 1 is shown again in FIG. 2 in an enlarged manner.

The enlarged cut-out 10 shows that the bottom of the pore 5 is formed by a layer 7 which is approximately 200 nm thick and arranged on the base material (iron-based alloy) of the implant body 1 and which consists of mixed oxides and mixed phosphates of the material of the metallic coating (tantalum and silver) and the base material (iron-based alloy). In contrast, the material of the plasmachemically generated layer 3 arranged lateral of the pore 5 is formed only from oxides and phosphates of the material of the metallic coating (tantalum and silver). It must be stressed again at this point that the pore bottom layer 7 and the pores 5 are integral parts of the plasmachemically generated layer 3.

The method for producing the plasmachemically generated layer includes for example the following steps:
  Contacting the stent body with a wire made of titanium.
  Immersing the stent body provided with the coating into the aqueous electrolyte with the following composition (aqueous basis):
  20 g/l ammonium carbonate (($NH_4$)$2CO_3.H_2O$)
  20 g/l potassium dihydrogen phosphate ($KH_2PO_4$)
  20 g/l sodium carbonate ($Na_2CO_3$)
  100 ml/l aqueous ammonia solution (25%)
  100 ml/l ethylenediamine ($C_2H_8N_2$).
  Applying a constantly increasing pulsed voltage from 0 V upwards, wherein the curve of the voltage corresponds to the curve designated above as pulsating or pulse voltage, and the stent body is connected as anode.
  The final voltage (maximum value of the peak voltage) of 500 V is reached after approx. 1 minute.
  The mean voltage is approx. 400 V since the lower bath voltage range is passed rapidly.
  Taking the stent body, which is now provided with the plasmachemically generated layer, out of the electrolyte and interrupting the contact in air, and
  Drying the stent as described above.

By means of the aqueous phosphate containing electrolyte, the surface of the implant body and the metallic coating are changed sectionally with respect to their chemical composition. In different depths relative to the surface of the metallic coating, different mixed tantalum and iron compounds are created as well as silver partially dissolved in the metallic matrix and metallic silver on the surface of the plasmachemically generated layer. The silver portion arranged on the surface has not been converted through the plasmachemical treatment. Said metallic silver with a proportion in the plasmachemically generated layer of <5% by mass acts antiproliferatively upon contact with body cells during the treatment of a human or an animal.

The stent treated in such a manner is subsequently crimped, mounted, inserted by means of a catheter for the treatment of a human or animal, and dilated, e.g. at the coronary destination site. Due to the strong adhesion of the plasmachemically modified tantalum to the iron bulk material, no layer delamination takes place during the dilatation process, and the corrosion can begin independently of the stent geometry and the respective zone of plastic deformation. The porous structure of the plasmachemically generated layer, which is present everywhere on the stent surface and which is accompanied by the presence of metallic or hydroxidic iron at the pore bottom, is now corroded, wherein the remaining tantalum acts as local element and iron as sacrificial anode. Due to the high characteristic corrosion resistance of tantalum, despite its low mass compared to iron, tantalum can act as local element during the entire degradation time. After a degradation time of approx. 12 months, the stent produced according to example 1 was metabolized (i.e. it loses its integrity after approx. 12 months) and any potentially remaining particles of metallic tantalum or other tantalum compounds were incorporated in the vessel wall without negative side effects. At the beginning of the degradation, the silver ions forming in this environment prevented effectively the formation of neointima and thus contributed substantially to a stable lumen over the lifetime of the stent.

Example 2

Figure 3:
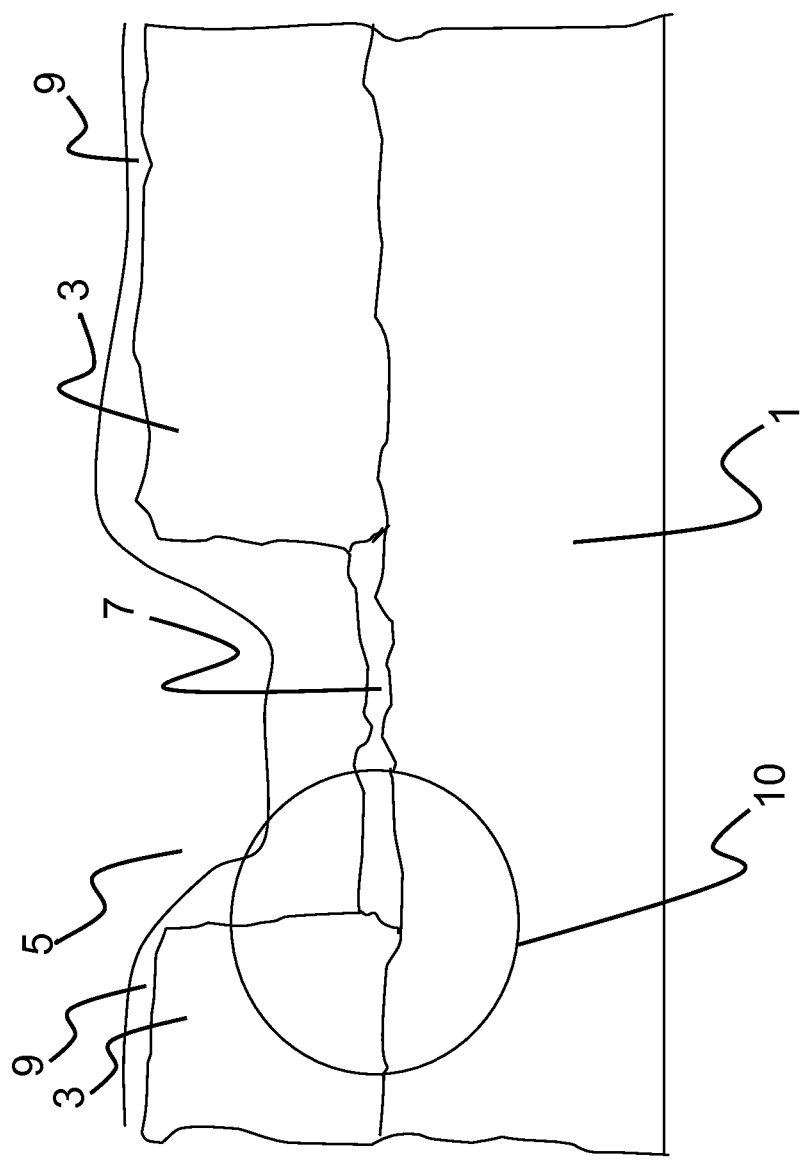
FIG. 3 shows a cross-section of the near-surface area of a web of a second exemplary embodiment of a stent according to the invention.

Example 2 corresponds to example 1 with the difference that the metallic coating is carried out only with tantalum (without silver). Further, after the plasmachemical treatment, the stent is additionally sprayed by means of known methods with a degradable, if applicable, acidic-degradable polymer, for example with PLGA 85/15 or PLLA L210. Here, a pharmaceutically active substance, for example paclitaxel or sirolimus, is incorporated in the polymer. A cross-section of a web having a polymer coating is illustrated in FIG. 3. The polymer layer has the reference number 9 and has a layer thickness of approximately 1 to 3 µm. The other layers shown in FIG. 3 correspond to the arrangement shown in FIG. 1.

The stent treated in such a manner is subsequently crimped, mounted, inserted by means of a catheter for the treatment of a human or animal, and dilated, e.g. at the coronary destination site. Due to the strong adhesion of the plasmachemically modified tantalum to the iron bulk material of the stent body, no layer delamination takes place during the dilatation process, and the corrosion can begin independently of the stent geometry and the respective zone of plastic deformation. The porous structure of the plasmachemically generated layer, which is present everywhere on the stent surface and which is accompanied by the presence of compounds of the iron (oxidic and/or hydroxidic an/or phosphatic) at the pore bottom, is now corroded, wherein the remaining tantalum acts as local element and iron as sacrificial anode.

At the beginning of the degradation process, the polymer layer acts as diffusion barrier for the corrosive medium. This means, first, a deceleration of the degradation process takes place. With increasing degradation of the polymer, a corrosion process is initiated which comes close to the one of example 1. However, the acidic degradation products of the polymer which are now present accelerate the process. The advantage of this example is therefore that the support effect of the stent is maintained longer at the beginning but decreases with progressing degradation faster than described in example 1. Nonetheless, a longer integral degradation time of approx. 15 months remains. Any potentially remaining particles of metallic tantalum or other tantalum compounds are incorporated in the vessel wall without negative side effects. Reference stents made of untreated iron have a degradation time of 24 months.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

REFERENCE NUMBER LIST

1 Implant base body
3 Plasmachemically generated layer
5 Pore
7 Pore bottom layer
9 Further layer
10 Cut-out

What is claimed is:

1. A method for producing an implant in the form of an intraluminal endoprosthesis, with a body, wherein the body contains iron or an iron alloy, comprising the following steps:
    a) providing the implant body,
    b) applying a metallic coating comprising as main constituent at least one element selected from the group consisting of tantalum, niobium, zirconium, aluminum, magnesium, vanadium, molybdenum, hafnium, and wolfram onto at least a portion of the body surface, and
    c) plasmachemical treatment of the portion of the body surface provided with the coating in an aqueous solution for producing a plasmachemically generated layer by means of applying a plasma-generating pulsating voltage to the body of the implant, wherein the pulsating voltage has sufficient energy that the metallic coating is temporarily and sectionally ionized up to the underlying implant body in such a manner that the generated layer has pores with an exposed bottom area composed of a mixture of oxides and phosphates of both the metallic coating and of the implant body.

2. The method according to claim 1, characterized in that the layer thickness of the metallic coating after completion of step b) is approximately 0.1 µm to approximately 1.5 µm.

3. The method according to claim 1, characterized in that the metallic coating is applied by means of an ionic liquid, by means of a PVD method, or by means of a CVD method.

4. The method according to claim 1, characterized in that the metallic coating has an additional element selected from the group consisting of copper and silver.

5. The method according to claim 1, characterized in that after step c), the implant is rinsed in a solvent and is subsequently dried at a temperature of at least approximately 80° C.

6. The method according to claim 1, characterized in that the aqueous solution contains $Sr^{2-}$ ions at a concentration of 0.05 Mol/l to 2.0 Mol/l $Sr^{2-}$.

7. The method according to claim 1, characterized in that the aqueous solution has one or more ions selected from the group consisting of phosphates, carbonates, and silicates, and/or that the aqueous solution comprises a buffer of potassium dihydrogen phosphate and/or sodium dihydrogen phosphate.

8. The method according to claim 1, characterized in that the plasmachemical treatment of the body surface is carried out in that to the body, a pulsed voltage is applied, the peak voltage of which during most of the treatment period exceeds at least approximately 400 Volt, and which increases in the course of the treatment up to approximately 500 V, wherein the current density during the plasmachemical treatment is at least approximately 5 $mA/cm^2$.

9. The method according to claim 1, characterized in that onto the plasmachemically generated layer, a further layer at least one polymer selected from the group consisting of parylene, PLA and its copolymers, PLLA and PLGA, is applied.

10. The method according to claim 5, wherein the solvent is distilled $H_2O$ and the temperature is at least approximately 100° C., wherein the drying is carried out in a convection oven.

11. The method according to claim 1, wherein the pores are arranged at geometrically regular distances.

12. The method according to claim 1, wherein that the pores have a density of approximately 50,000 pores/$mm^2$ to approximately 250,000 pores/$mm^2$.

* * * * *